(12) United States Patent
Furst et al.

(10) Patent No.: US 6,436,133 B1
(45) Date of Patent: Aug. 20, 2002

(54) EXPANDABLE GRAFT

(76) Inventors: Joseph G. Furst, 1530 Richmond Rd., Lyndhurst, OH (US) 44124; Rassoll Rashidi, 10301 Lake Ave., #402 Box 1940, Cleveland, OH (US) 44106

( * ) Notice: Subject to any disclaimer, the term of this patent is extended or adjusted under 35 U.S.C. 154(b) by 0 days.

(21) Appl. No.: 09/273,736

(22) Filed: Mar. 22, 1999

Related U.S. Application Data

(60) Provisional application No. 60/081,824, filed on Apr. 15, 1998.

(51) Int. Cl.$^7$ .................................................. A61F 2/06
(52) U.S. Cl. ...................................................... 623/1.15
(58) Field of Search ........................... 606/1, 108, 195, 606/198, 200, 194; 623/1.1, 1.11, 1.15, 1.16, 1.17, 12

(56) References Cited

U.S. PATENT DOCUMENTS

| | | | |
|---|---|---|---|
| 4,733,665 A | | 3/1988 | Palmaz |
| 4,739,762 A | | 4/1988 | Palmaz |
| 4,776,337 A | | 10/1988 | Palmaz |
| 5,102,417 A | | 4/1992 | Palmaz |
| 5,195,984 A | | 3/1993 | Schatz |
| 5,316,023 A | | 5/1994 | Palmaz et al. |
| 5,571,170 A | | 11/1996 | Palmaz et al. |
| 5,725,572 A | * | 3/1998 | Lam et al. .................. 623/1.34 |
| 5,735,871 A | * | 4/1998 | Sgro .......................... 606/198 |
| 5,755,781 A | * | 5/1998 | Jayaraman .................. 623/1.1 |
| 5,853,419 A | * | 12/1998 | Imran ......................... 623/1.15 |
| 5,861,027 A | * | 1/1999 | Trapp .......................... 606/198 |
| 5,879,370 A | * | 3/1999 | Fischell et al. ............. 623/1.16 |
| 5,911,732 A | * | 6/1999 | Hojeibane .................. 623/1.11 |
| 5,964,798 A | * | 10/1999 | Imran ......................... 623/1.16 |
| 5,968,091 A | * | 10/1999 | Pinchuk et al. ............. 623/1.11 |
| 6,007,573 A | * | 12/1999 | Wallace et al. ............. 606/194 |
| 6,059,810 A | * | 5/2000 | Brown et al. ............... 606/198 |
| 6,200,337 B1 | * | 3/2001 | Moriuchi et al. ........... 623/1.16 |

FOREIGN PATENT DOCUMENTS

| | | | |
|---|---|---|---|
| EP | 4 433 011 | * | 6/1991 |
| EP | 0 836 839 A2 | | 4/1998 |
| WO | WO 99/56663 | | 11/1999 |

OTHER PUBLICATIONS

"Progress in Cardiovascular Diseases" vol. XXXIX, No. 2, Sep./Oct. 1996.
USCI brochure entitled "PE Plus Peripheral Balloon Dilatation Catheter" Aug. 1985.

* cited by examiner

*Primary Examiner*—Kevin T. Truong
(74) *Attorney, Agent, or Firm*—Vickers, Daniels & Young

(57) ABSTRACT

An expandable intraluminal graft for use within a body cavity having a tubular shaped member with two ends and a wall surface disposed between the ends. The wall surface is formed by a plurality of intersecting elongated members wherein the elongated members intersecting with one another intermediate the ends of the tubular shaped member. The tubular shaped member has a first diameter to permit intraluminal delivery of the member into a body cavity, and a second variable expanded diameter.

64 Claims, 5 Drawing Sheets

EXPANDABLE GRAFT

This application claims benefits of provisional application 60/081,824 filed Apr. 15, 1998.

This invention relates to an improved expandable intraluminal graft for use within a body passageway, duct, blood vessel or other cavity and, more particularly, expandable intraluminal grafts which are particularly useful for repairing blood vessels narrowed or occluded by disease. Here after the terms graft and stent are interchangeable.

BACKGROUND OF THE INVENTION

Heart disease is still one of the most prevalent medical ailment in the world. Intraluminal endovascular grafting, a type of angioplasty procedure, has been demonstrated by experimentation to present a possible alternative to conventional vascular surgery and is used to treat heart disease. Intraluminal endovascular grafting involves a tubular prosthetic graft and its' delivery within the vascular system. Advantages of this method over conventional vascular surgery include obviating the need for surgically exposing, incising, removing, replacing, or bypassing the defective blood vessel. Almost 20 million angioplasty or related procedures involving occluded vasculature have been preformed worldwide. About 30% of these angioplasties fail within 30 days. These failures typically require the procedure to be repeated.

Several years ago, a product called a stent, named after Charles Stent, was introduced for use in angioplasty procedures. The stent reduced the angioplasty failure rate to about 15 percent. A stent is an expandable metal tubular device that is mounted over an angioplasty balloon and deployed at the site of coronary narrowing. The balloon is inflated to expand the stent so as to physically open and return patency to the body passageway, duct or blood vessel. The balloon is then deflated and the stent is permanently disposed to retain the passageway, duct or blood vessel open. The first generation of expandable stents did not offer a controllable radial expansion. An improved stent is disclosed in United States Letters Patent No. 4,733,665. The stent disclosed in the '665 patent overcame the problem associated with controlled expansion of the stent. In prior art, there was no control over the final, expanded configuration of the stent. For instance, the expansion of a particular coiled spring-type stent was predetermined by the method of manufacturing, material and delivery system. In the case of self-expanding intraluminal grafts, or prostheses, formed of a heat sensitive material which expands upon exposure to core body temperature, the amount of expansion was predetermined by the heat expansion properties of the particular alloy utilized in the manufacture of the intraluminal graft. Thus, once the foregoing types of intraluminal grafts were expanded at the desired location within a body passageway, such as within an artery or vein, the expanded size of the graft can not be increased. If the diameter of the desired narrow lumened body passageway had not been determined correctly, the graft might not expand enough to contact the interior surface of the body passageway, so as to be secured thereto. The stent disclosed in the '665 patent overcame the problems associated with these past stent designs.

The stent based upon the '665 patent is currently being used in angioplasty procedures. Stents, including the stent of the '665 patent, are presently used in approximately 30–60 percent of all angioplasty procedures. However, these stents have several other short comings which contribute to the procedural failure rates. The currently used stents are not readily visible under fluoroscopic guidance procedurally. Stent placement is hindered as a result of poor visibility. These stents of prior art also shorten longitudinally after radial expansion, which is not desirable for its' intended use.

In view of the present stent technology, there is a need and demand for a stent that has improved procedural success rates, has higher viability under fluoroscopy in vivo and retains its' longitudinal dimensions from its' original pre-expanded configuration to the expanded state.

SUMMARY OF THE INVENTION

This invention pertains to an improved expandable intraluminal graft that is designed to meet the present day needs and demands relating to intraluminal grafts. The present invention includes a tubular shaped member having first and second ends and a wall surface disposed between the first and second ends, the wall surface being formed by a plurality of intersecting elongated members, at least some of the elongated members intersecting with one another intermediate the first and second ends of the tubular shaped member; the tubular shaped member having a first diameter which permits intraluminal delivery of the tubular shaped member into a body passageway having a lumen; and the tubular shaped member having a second, expanded diameter, upon the application from the interior of the tubular shaped member of a radially, outwardly extending force, which second diameter is variable and dependent upon the amount of radially outward force applied to the tubular shaped member, whereby the tubular shaped member may be expanded to expand the lumen of the body passageway while retaining its original length.

Another feature of the present invention is that the plurality of elongated members may be a plurality of wires, and the wires may be fixedly secured to one another where the wires intersect with one another.

Yet another feature of the present invention is that the plurality of elongated members may be a plurality of thin bars which are fixedly secured to one another where the bars intersect with one another.

Still yet another feature of the present invention is that the elongated members form a plurality of parallelograms which upon expansion, retain the original longitudinal length of the graft.

Another feature of the present invention is that the graft includes two sets of slots arranged with respect to one another to maintain the original longitudinal length of the graft when the graft is expanded.

Yet another feature of the present invention is that the graft is formed by an etching process and/or by laser cutting.

Still another feature of the present invention is that the intraluminal graft member may have a biologically inert coating on its wall surface. The coating can be used to reduce infection, irritation and/or rejection of the intraluminal graft.

Still yet another feature of the present invention is that the intraluminal graft, upon expansion, substantially maintains its original longitudinal length.

Another feature of the present invention is that the intraluminal graft includes at least two tubular members that are connected together by at least one connector that allows transverse bending and flexibility invariant to the plane of bending.

Still another feature of the present invention is that the connector is a "U" shaped connector.

Yet another feature of the present invention is that the tubular shaped member is made of and/or includes a material that is more visible under fluoroscopy in vivothan currently available stents. The tubular member may include a special material such as gold to enhance the visibility of the tubular member in a body passageway, duct, blood vessel, etc..

Still yet another feature of the present invention is the material to make the tubular member visible under fluoroscopy. Preferably, this is accomplished by adhering, mounting, welding or abrasing a second material to the outer surface of the tubular member so as to only come in contact with the inner luminal surface of the vessel and not any blood borne components that could accelerate stent failure rates.

Another feature of the present invention is the material used to make the tubular member visible under fluoroscopy is located on the outer surface of the tubular member located at both ends of the tubular member. This shows were the tubular member both begins and ends thus enhancing the critical placement of the stent so as not to accelerate the failure rate.

Yet another feature of the present invention is the material used to make the tubular member visible under fluoroscopy. is located on the outer surface of the tubular member at the connecting flexible joints of the tubular member at any position between the two ends. This also enhances the critical placement of the stent around areas of high tortuosity so as not to accelerate the failure rate.

Still another feature of the present invention is the material is treated with Gamma or Beta radiation to reduce the vascular narrowing of the stented section. The radioactive treatment inactivates the cell migration and properties thereof within a 3 mm depth of the arterial wall.

Still yet another feature of the present invention is that a wire mesh tube may be utilized as the intraluminal graft. The wire mesh tube can be radially expanded to a second diameter within the body passageway; the second, expanded diameter being variable and determined by the desired expanded internal diameter of the body passageway, duct, blood vessel, etc, whereby the expanded wire mesh tube will not migrate from the desired location within the body passageway, duct, blood vessel, etc. and the expansion of the intraluminal graft does not cause a rupture of the body passageway, duct, blood vessel, etc.

Another feature of the present invention is that the intraluminal graft can be inserted and expanded by standard procedures. Therefore, the intraluminal graft can be inserted into a body passageway, duct, blood vessel, etc. until it is disposed at the desired location within the body passageway. The intraluminal graft is radially expanded outwardly into contact with the body passageway until the lumen of the body passageway at the desired location, luminal narrowing, has been expanded, whereby the intraluminal graft prevents the body passageway from collapsing. In summary, the present invention includes a radially expandable, tubular shaped prosthesis having first and second ends and a wall surface disposed between the first and second ends, the wall surface being formed by a plurality of intersecting elongated members and whose longitudinal structure remains the same from its original pre-expanded length after radial expansion.

BRIEF DESCRIPTION OF THE DRAWINGS

Reference may now be made to the drawings, which illustrate various embodiments that the invention may take in physical form and in certain parts and arrangements of parts wherein.

DETAILED DESCRIPTION OF THE INVENTION

Figure 1:
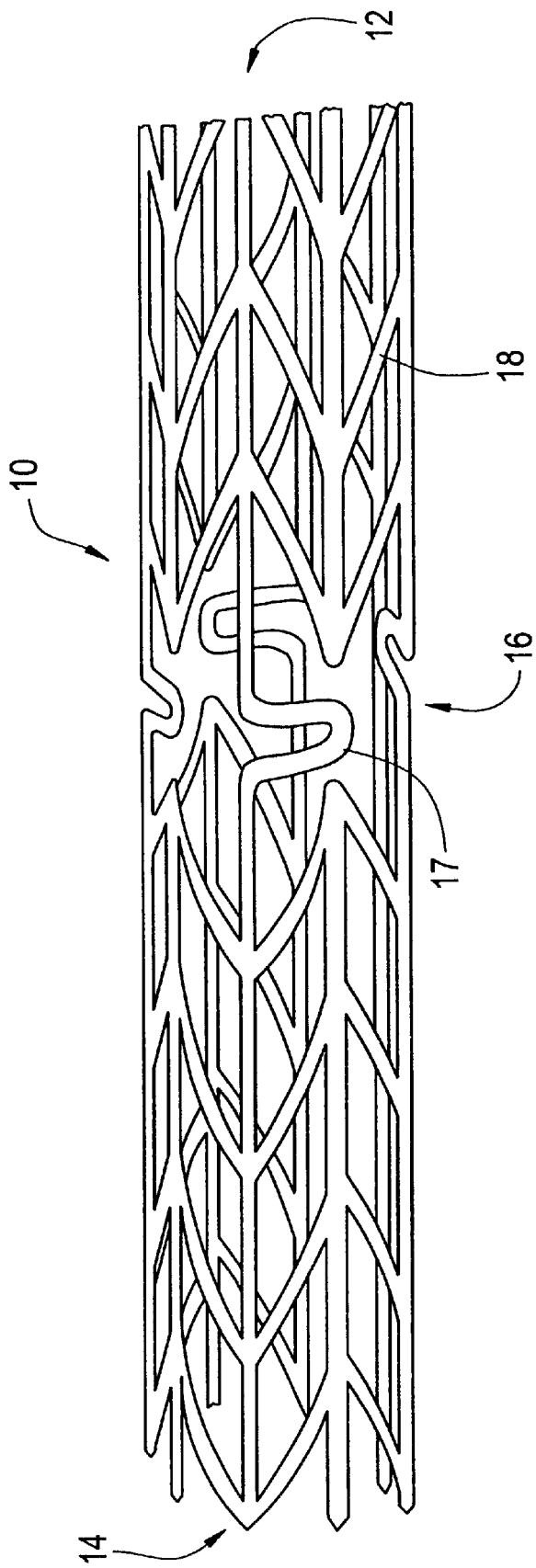
FIG. 1 is a perspective view of an expandable intraluminal graft which permits delivery of the graft, or prosthesis, into a body passageway.

Referring now to the drawings wherein the showing is for the purpose of illustrating preferred embodiments of the invention only and not for the purpose of limiting the same, the figures disclose an expandable intraluminal graft, or expandable prosthesis for a body passageway. It should be understood that the terms "expandable intraluminal graft" and "expandable prosthesis" are interchangeably used to some extent in describing the present invention, insofar as the apparatus and structures of the present invention may be utilized not only in connection with an expandable intraluminal graft for expanding partially occluded segments of a blood vessel, or body passageway. For example, the expandable prostheses may also be used for such purposes as supportive graft placement within blocked vasculature opened by transluminal recanalization, but which are likely to collapse in the absence of an internal support; forming a catheter passage through mediastinal and other veins occluded by inoperable cancers; reinforcement of catheter created intrahepatic communications between portal and hepatic veins in patients suffering from portal hypertension; supportive graft placement of narrowing of the esophagus, the intestine, the ureter, the urethra; and supportive graft reinforcement of reopened and previously obstructed bile ducts. Accordingly, use of the term "prosthesis" encompasses the foregoing usages within various types of body passageways, and the use of the term "intraluminal graft" encompasses use for expanding the lumen of a body passageway. Further, in this regard, the term "body passageway" encompasses any duct within the human body, such as those previously described, as well as any vein, artery, or blood vessel within the human vascular system.

Figure 4:
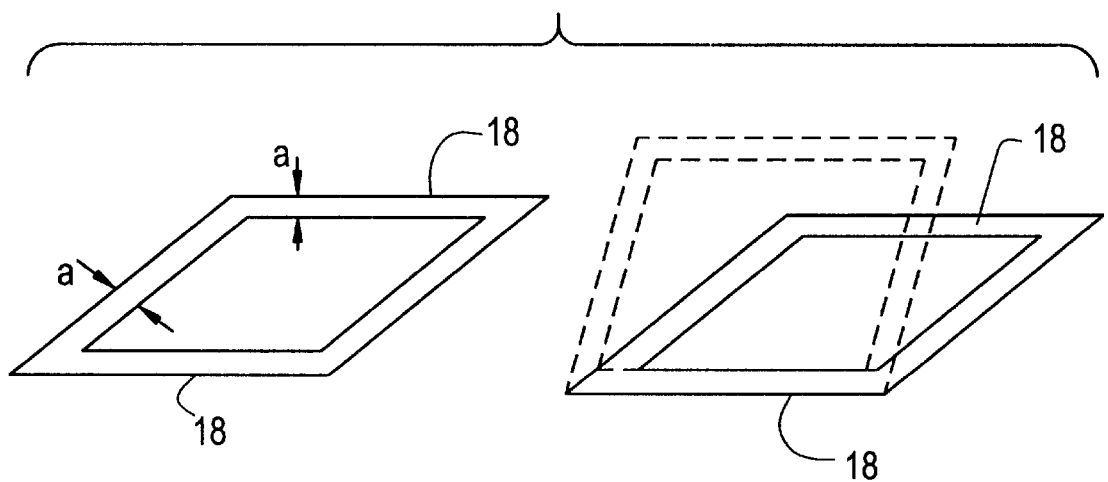
FIG. 4 is a sectional view of the graft of FIG. 2 showing the parallelogram structure of the graft before and after expansion.

The expandable intraluminal graft as shown in the FIGS. 1, 2, 3 and 4 generally comprises a tubular shaped member 10 having first end 12 and second end 14 and a wall surface 16 disposed between the first and second ends. Preferably, the wall surface is formed by a plurality of intersecting elongated members 18 with at least some of the elongated members intersecting with one another intermediate the first and second ends of the tubular shaped member. The tubular shaped member has a first diameter which permits intraluminal delivery of the tubular shaped member into a body passageway having a lumen. FIG. 4 shows a perspective view of the tubular shaped member 10 which has a second, expanded diameter, which second diameter is variable in size.

Figure 2:
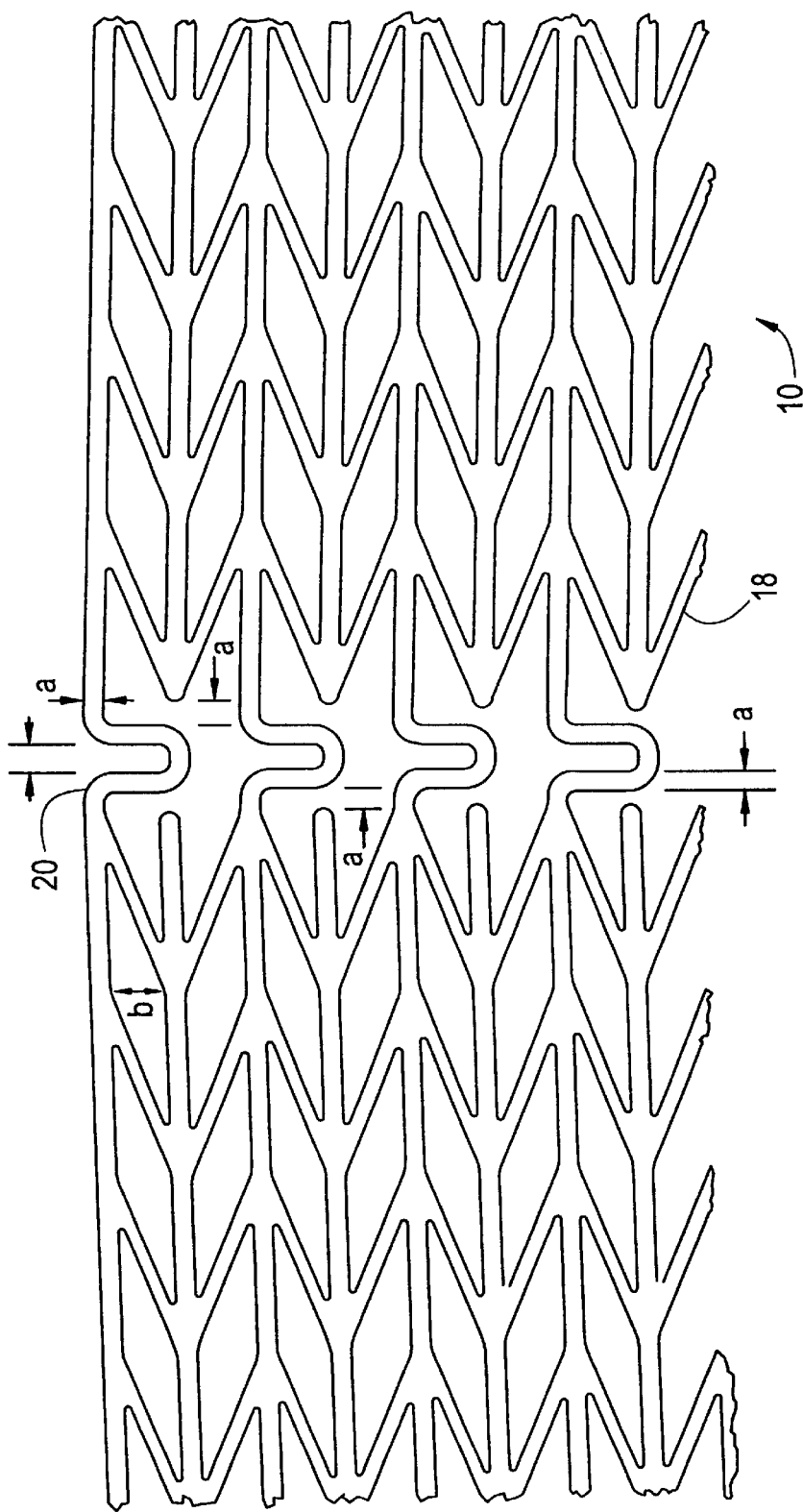
FIG. 2 is a perspective view of the graft of FIG. 1 in a non-tubular state.
Figure 3:
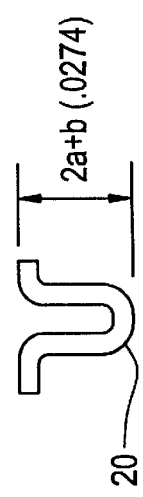
FIG. 3 is a sectional view of the graft of FIG. 2 showing a connector use to connect the ends of two tubular sections of the graft.

The elongated members 18, which form wall surface of the tubular shaped member may be any suitable material which is compatible with the human body and the bodily fluids with which the graft, or prosthesis, may come into contact. Preferably the elongated members are made of a material or include a material that is readily visible in vivo under fluoroscopic view. The elongated members also are made of a material which has the requisite strength and elasticity characteristics to permit the tubular shaped member to be expanded from its original tubular form, to its expanded tubular form, and to further to permit the tubular shaped member to retain its expanded configuration with the enlarged diameter. Suitable materials for the fabrication the of tubular shaped structure of include tantalum, stainless steel, titanium or any suitable plastic material having the requisite characteristics previously described. The elongated members 18 are small diameter, about 0.005 inches, wires or bars. It should of course be understood that each elongated member could have any cross-sectional configurations, such as triangular, square, rectangular, hexagonal, etc. Further, it is preferable that the plurality of elongated members are fixedly secured to one another with a "U" shaped member 17 where the elongated members 18 join with one another. Preferably, the elongated members are formed by etching a single tubular piece of material so that each individual intersection need not be welded. For example, a tubular shaped member is initially a thin-walled metal tube, and the openings between the intersecting bars are formed by a conventional etching process, such as electromechanical or laser etching, whereby the resultant structure is a tubular shaped member having a plurality of intersecting elongated members as shown in FIGS. 1 and 2. This technique enhances the structural integrity of the tubular structure and reduces the number of rough surfaces at the intersection points. Preferably, tubular shaped structure of is made of stainless steel.

The particular design of the pattern is shown in the FIGS. 1 and 2. The openings between the intersecting bars are preferably parallelogram in shape. The openings are positioned to form a pattern as shown in the FIG. 4. As can be appreciated, this parallelogram pattern allows the tubular shaped members to be expanded without the members having a reduction in length in the longitudinal direction. Since a parallelogram is a four sided figure with opposite sides parallel. As the angle of the parallelogram changes, the sides that are elongated with the longitudinal axis of structure of member 18 will remain the same. Preferably, the surface of the tubular member is formed by pluralities of parallelograms.

As shown in FIG. 1, is the improved arrangement for connecting two tubular members 18 by at least one "U" shaped member 17 together to increase the flexibility of the graft. The connector is shown to be a "U" shaped member 17 that connects two ends of the tubular members 18 together. As shown in the Figures, pluralities of "U" shaped members 17 are used to connect a set of two adjacently positioned ends of one tubular member to a corresponding set of adjacently positioned ends in the other tubular member. This configuration allows at least two tubular members that are connected together by at least one set of circularly distributed "U" shaped connector that allows transverse bending and flexibility invariant to the plane of bending.

Figure 8:
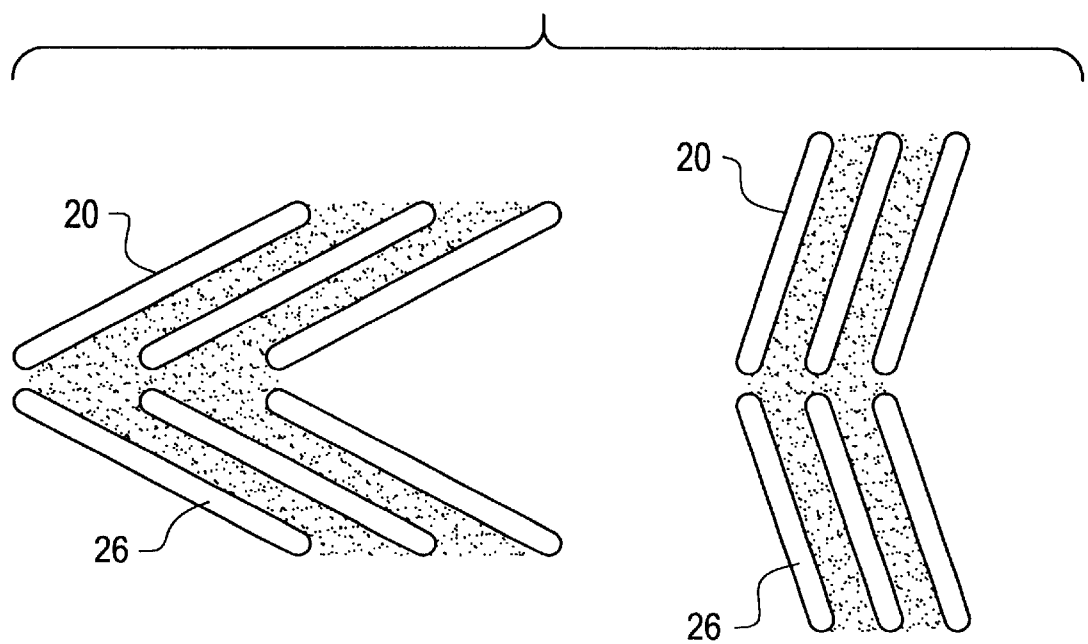
FIG. 8 is a sectional view of the graft of FIG. 5 showing a part of the structure of the graft before and after expansion.
Figure 5:
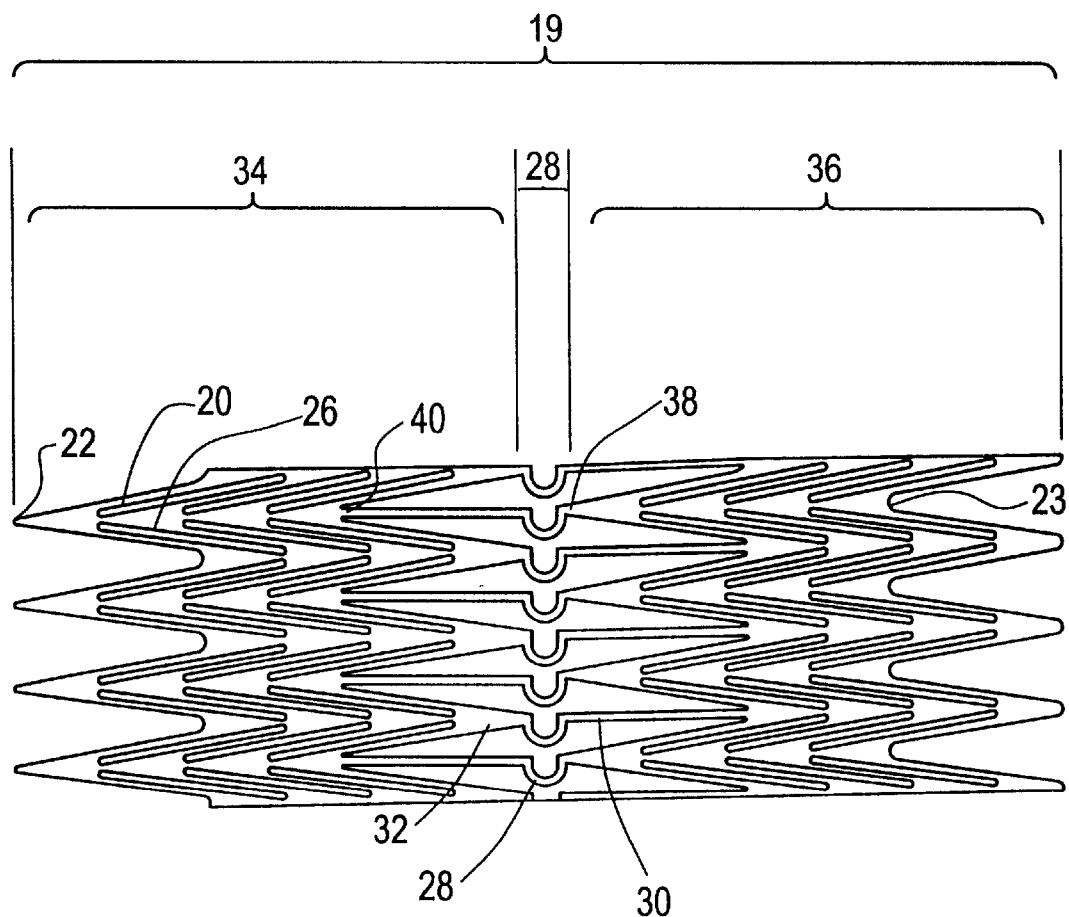
FIG. 5 is a perspective view of an additional embodiment of the present invention.
Figure 6:
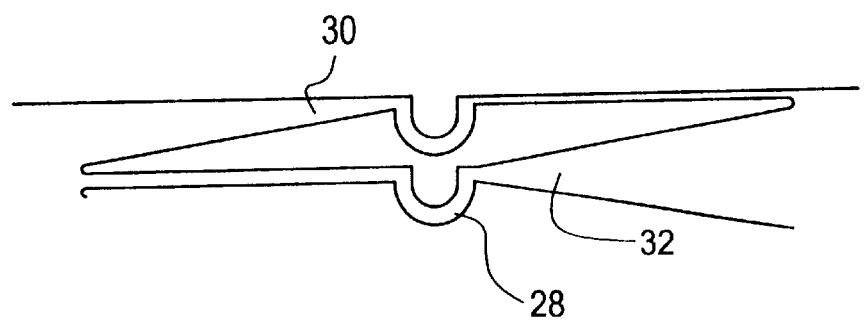
FIG. 6 is a sectional view of the graft of FIG. 5 showing a connection used to connect the ends of two sections of the graft together.
Figure 7:
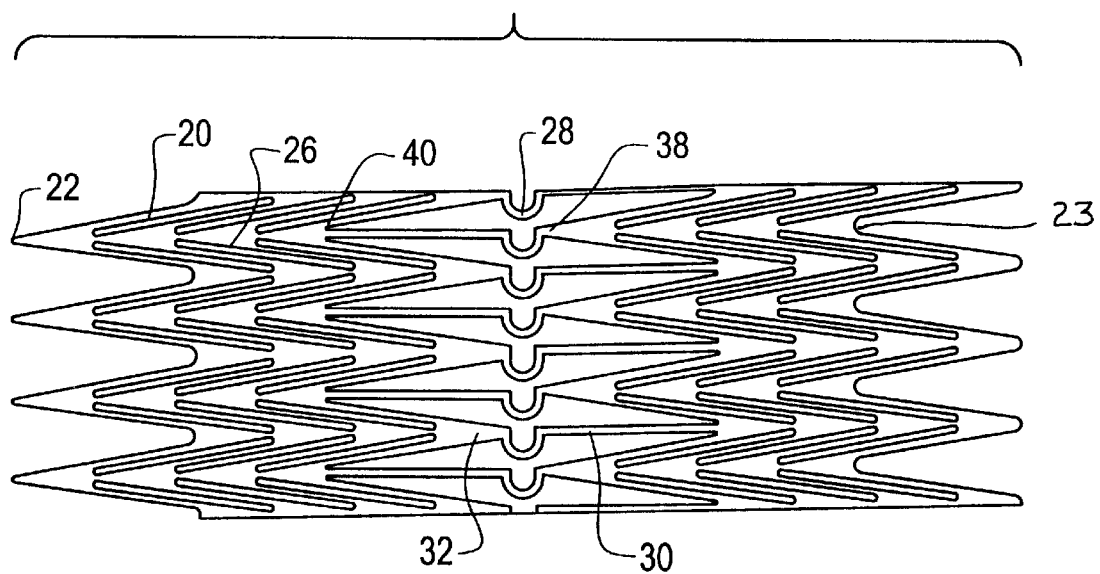
FIG. 7 is a section view of the graft of FIG. 5 showing the location and angular orientation of opening in the graft.
Figure 7:
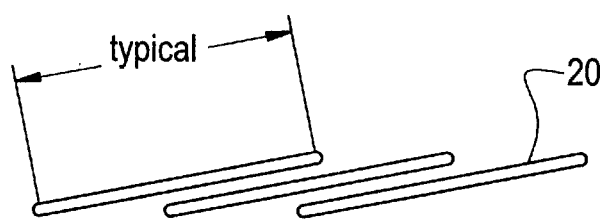

Referring now to FIGS. 5, 6, 7 and 8, a second embodiment of the present invention. As shown in FIG. 5, a graft 19 includes two sections 34, 36. However, graft 19 may include more than two sections. The two sections 34, 36 are connected together by a connector 28. Preferably, connector 28 is arcuate in shape and more preferably is "U" shaped. As shown in FIG. 5, sections 34, 36 are substantially symmetrical to one another and preferably have substantially identical dimensions. Each section includes a plurality of slots 20, 26. Slots 20, 26 are preferably equal in length and width. The series of slots 20 are arranged substantially parallel to one another. The series of slots 26 are also arranged substantially parallel to one another. Slots 20 and 26 are positioned relative to one another to form an angle between 0–90° when the graft is in the unexpanded position as shown in FIG. 5. The slot arrangement between ends 22 and 23 of graft 19 allow the graft, when expanded radially, to retain its originally pre-expanded length. The configuration of the slots 20, 26 in the pre-expanded and post-expanded position is shown in FIG. 8. The formation of slots 20, 26 by use of a laser is shown in FIG. 7. However, the slots can be formed by other means. The configuration of connectors 28 is shown in FIG. 6.

The present invention has been described with reference to a number of different embodiments. It is to be understood that the invention is not limited to the exact details of construction, operation, exact materials or embodiment shown and described, as obvious modifications and equivalents will be apparent to one skilled in the art. It is believed that many modifications and alterations to the embodiments disclosed will readily suggest themselves to those skilled in the art upon reading and understanding the detailed description of the invention. It is intended to include all such modifications and alterations insofar as they come within the scope of the present invention.

What is claimed is:

1. An expandable intraluminal graft for use within in a body passageway, duct, blood vessel or other cavity comprising:

a plurality of substantially tubular shaped members and at least one connector connecting at least two tubular shaped members, each of said tubular shaped members having first and second ends and a wall surface disposed between the first and second ends, the wall surface of each tubular shaped member being formed by a plurality of intersecting elongated members, at least some of the elongated members intersecting. with one another intermediate the first and second ends of the tubular shaped members, said plurality of intersecting elongated members forming a plurality of openings in said wall surface;

each of said tubular shaped members having a first diameter which permits intraluminal delivery of the tubular shaped members into a body passageway, duct, blood vessel or other cavity, and a second expanded diameter which second diameter is variable, each of said tubular shaped members having substantially the same longitudinal length when said members are in their first diameter and in their said second diameter, at least two of said openings in said wall surface of each of said tubular shaped members having a parallelogram shape when said members are in their first diameter;

said connector allowing transverse bending flexibility invariant to the plane of bending of said graft, at least one of said connectors being substantially "U" shaped.

2. The expandable intraluminal graft of claim 1, wherein the plurality of elongated members are a plurality of wires, and the wires are fixedly secured to one another where the wires intersect with one another.

3. The expandable intraluminal graft of claim 2, wherein at least one of said tubular shaped members including material to make said at least one tubular shaped member visible under fluoroscopy.

4. The expandable intraluminal graft of claim 3, wherein said at least one tubular member is treated with radiation to reduce the vascular narrowing of the stented section, said radiation including Gamma radiation, Beta radiation, and combinations thereof.

5. The expandable intraluminal graft of claim 4, including a plurality of said connectors.

6. The expandable intraluminal graft of claim 1, wherein the plurality of elongated members are a plurality of thin bars which are fixedly secured to one another where the bars intersect with one another.

7. The expandable intraluminal graft of claim 6, wherein at least one of said tubular shaped members including material to make said at least one tubular shaped member visible under fluoroscopy.

8. The expandable intraluminal graft of claim 1, wherein at least one of said tubular shaped members including material to make said at least one tubular shaped member visible under fluoroscopy.

9. The expandable intraluminal graft of claim 8, wherein said material used to make at least one of said tubular shaped members visible under fluoroscopy is located on the outer surface of said at least one tubular shaped member and located at both ends of said at least one tubular shaped member.

10. The expandable intraluminal graft of claim 8, wherein said material used to make at least one of said tubular shaped members visible under fluoroscopy is located on the outer surface of said at least one tubular shaped member and at any position between said two ends.

11. The expandable intraluminal graft of claim 1, wherein said at least one tubular member is treated with radiation to reduce the vascular narrowing of the stented section, said radiation including Gamma radiation, Beta radiation, and combinations thereof.

12. The expandable intraluminal graft of claim 1, wherein said intersecting elongated members are at least partially formed by a process including etching, laser cutting, and combinations thereof.

13. The expandable intraluminal graft of claim 1, including a plurality of said connectors.

14. An expandable intraluminal graft for use within a body passageway, duct, blood vessel or other cavity comprising:
a substantially tubular shaped member formed from a single piece of material having first and second ends and a wall surface disposed between the first and second ends defining a longitudinal length of said tubular body member, said wall surface including a first and second set of slots about a circumference of said tubular body member, each set of slots including at least two slots positioned substantially parallel to one another along said longitudinal length of said tubular body member;
said tubular shaped member having a first diameter which permits intraluminal delivery of said tubular shaped member into a body passageway, duct, blood vessel or other cavity, and a second expanded diameter which second diameter is variable, said tubular shaped member having substantially the same longitudinal length when said tubular shaped member is in its first diameter and in its said second diameter, said first set of slots not parallel to a longitudinal axis of said tubular shaped member when said tubular shaped member is in said first diameter, said first and said second set of slots forming an angle between said sets of slots between 0–90° when said tubular shaped member is in said first diameter.

15. The expandable intraluminal graft of claim 14, having at least one connector and two tubular shaped members, said connector connected between said two tubular shaped members, said connector allowing transverse bending flexibility invariant to the plane of bending of said graft.

16. The expandable intraluminal graft of claim 15, wherein said connector is substantially "U" shaped.

17. The expandable intraluminal graft of claim 16, including a plurality of said connectors.

18. The expandable intraluminal graft of claim 15, including a plurality of said connectors.

19. The expandable intraluminal graft of claim 14, wherein said tubular shaped member having material to make the tubular member visible under fluoroscopy.

20. The expandable intraluminal graft of claim 19, wherein said material used to make the tubular member visible under fluoroscopy is located on the outer surface of said tubular shaped member and located at both ends of said tubular shaped member.

21. The expandable intraluminal graft of claim 19, wherein said material used to make said tubular shaped member visible under fluoroscopy that is located on the outer surface of said tubular shaped member and at any position between the two ends.

22. The expandable intraluminal graft of claim 14, wherein said tubular shaped member is treated with radiation to reduce the vascular narrowing of the stented section, said radiation including Gamma radiation, Beta radiation, and combinations thereof.

23. The expandable intraluminal graft of claim 14, wherein said intersecting elongated members are at least partially formed by a process including etching, laser cutting, and combinations thereof.

24. The expandable intraluminal graft of claim 14, wherein said second set of slots is not parallel to said longitudinal axis of said tubular shaped member when said tubular shaped member is in said first diameter.

25. The expandable intraluminal graft of claim 24, wherein said first and second set of slots are not parallel to said longitudinal axis of said tubular shaped member when said tubular shaped member is in said second diameter.

26. The expandable intraluminal graft of claim 14, wherein said second set of slots is not parallel to said longitudinal axis of said member when said tubular shaped member is in said first diameter.

27. The expandable intraluminal graft of claim 26, wherein said first and second set of slots are not parallel to said longitudinal axis of said member when said tubular shaped member is in said second diameter.

28. The expandable intraluminal graft of claim 27, wherein a plurality of said slots of said one set of slots include first and second ends, at least two adjacently positioned slots having said first and said second ends, said first ends of said slots lying in a first plane substantially parallel to a longitudinal axis of said tubular shaped member when said tubular shaped member is in said first diameter, said second ends of said slots lying in a second plane substantially parallel to a longitudinal axis of said tubular shaped member when said tubular shaped member is in said first diameter.

29. An expandable intraluminal graft for use within in a body passageway, duct, blood vessel or other cavity comprising:
a plurality of body members and at least one connector connecting at least two of said body members, each of said body members having first and second ends and a wall surface disposed between the first and second ends, the wall surface being formed by a plurality of intersecting elongated members, at least some of the elongated members intersecting with one another intermediate the first and second ends of each of said body members and forming a plurality of segments, at least two of said segments formed of at least four intersecting elongated members which define the top, bottom and two sides of said segment, said two sides are non-parallel to a longitudinal axis of each of said body members;

each of said body members having a first diameter which permits intraluminal delivery of said body members into a body passageway, duct, blood vessel or other cavity, and a second expanded diameter which second diameter is variable, each of said body members having substantially the same longitudinal length when said members are in their first diameter and in their said second diameter, said two sides of said segments being substantially parallel to one another in said first and said second diameter of said body members;

said connector allowing transverse bending flexibility invariant to the plane of bending of said body members, at least one of said connectors being substantially "U" shaped.

30. The expandable intraluminal graft of claim 29, wherein said top and said bottom elongated members being substantially parallel to one another in said first and said second diameter of said body members.

31. The expandable intraluminal graft of claim 30, wherein said top and said bottom elongated members are substantially parallel to said longitudinal axis of said body members.

32. The expandable intraluminal graft of claim 29, wherein said top and said bottom elongated members are substantially parallel to said longitudinal axis of said body members.

33. The expandable intraluminal graft of claim 29, wherein at least one of said body members is a substantially tubular shaped member.

34. The expandable intraluminal graft of claim 29, wherein the plurality of elongated members are a plurality of wires, and the wires are fixedly secured to one another where the wires intersect with one another.

35. The expandable intraluminal graft of claim 29, wherein the plurality of elongated members are a plurality of thin bars which are fixedly secured to one another where the bars intersect with one another.

36. The expandable intraluminal graft of claim 29, wherein at least one of said segments being substantially parallelogram shaped.

37. The expandable intraluminal graft of claim 29, wherein said at least one of said body members having material to make said body member visible under fluoroscopy.

38. The expandable intraluminal graft of claim 37, wherein said material used to make said body member visible under fluoroscopy is located on the outer surface of said body member at both ends of said body member.

39. The expandable intraluminal graft of claim 29, wherein at least a portion of at least one of said body members is treated with radiation, said radiation including Gamma radiation, Beta radiation, and combinations thereof.

40. The expandable intraluminal graft of claim 29, wherein at least one of said segments being substantially parallelogram shaped.

41. The expandable intraluminal graft of claim 40, wherein said at least one of said body members having material to make said body member visible under fluoroscopy.

42. The expandable intraluminal graft of claim 41, wherein at least a portion of at least one of said body members is treated with radiation, said radiation including Gamma radiation, Beta radiation, and combinations thereof.

43. The expandable intraluminal graft of claim 42, wherein the plurality of elongated members are a plurality of wires, and the wires are fixedly secured to one another where the wires intersect with one another.

44. The expandable intraluminal graft of claim 43, wherein at least one of said body members is a substantially tubular shaped member.

45. The expandable intraluminal graft of claim 44, including a plurality of said connectors.

46. The expandable intraluminal graft of claim 42, wherein the plurality of elongated members are a plurality of thin bars which are fixedly secured to one another where the bars intersect with one another.

47. The expandable intraluminal graft of claim 46, wherein at least one of said body members is a substantially tubular shaped member.

48. The expandable intraluminal graft of claim 47, including a plurality of said connectors.

49. The expandable intraluminal graft of claim 29, including a plurality of said connectors.

50. An expandable intraluminal graft for use within a body passageway, duct, blood vessel or other cavity comprising:

a body member formed from a single piece of material having first and second ends and a wall surface disposed between the first and second ends defining a longitudinal length of said body member, said wall surface including a first and second set of slots about an outer perimeter of said body member, each set of slots including at least two slots positioned substantially parallel to one another along said longitudinal length of said body member;

said body member having a first diameter which permits intraluminal delivery of said body member into a body passageway, duct, blood vessel or other cavity, and a second expanded diameter which second diameter is variable, said body member having substantially the same longitudinal length when said body member is in its first diameter and in its second diameter, said first set of slots not parallel to a longitudinal axis of said body member when said body member is in said first diameter, said first and said second set of slots forming an angle between said sets of slots between 0–90° when said body member is in said first diameter.

51. The expandable intraluminal graft of claim 50, wherein a plurality of said slots of said one set of slots include first and second ends, at least two adjacently positioned slots having said first and said second ends, said first ends of said slots lying in a first plane substantially parallel to a longitudinal axis of said body member when said body member is in said first diameter, said second ends of said slots lying in a second plane substantially parallel to a longitudinal axis of said body member when said body member is in said first diameter, said first and second set of slots are not parallel to said longitudinal axis of said body member when said body member is in said first diameter.

52. The expandable intraluminal graft of claim 51, wherein a plurality of said slots of said one set of slots include first and second ends, at least two adjacently positioned slots having said first and said second ends, said first ends of said slots lying in a first plane substantially parallel to a longitudinal axis of said body member when said body member is in said second diameter, said second ends of said slots lying in a second plane substantially parallel to a longitudinal axis of said body member when said body member is in said second diameter.

53. The expandable intraluminal graft of claim 50, wherein a plurality of said slots of said one set of slots include first and second ends, at least two adjacently positioned slots having said first and said second ends, said first ends of said slots. lying in a first plane substantially parallel to a longitudinal axis of said body member when said body member is in said second diameter, said second ends of said slots lying in a second plane substantially parallel to a longitudinal axis of said body member when said body member is in said second diameter, said first and second set of slots are not parallel to said longitudinal axis of said body member when said body member is in said second diameter.

54. The expandable intraluminal graft of claim 50, wherein said body member is a substantially tubular shaped member.

55. The expandable intraluminal graft of claim 50, wherein said material used to make the body visible under fluoroscopy is located on the outer surface of said body member at both ends of said body member.

56. The expandable intraluminal graft of claim 50, wherein at least a portion of said body member is treated with radiation, said radiation including Gamma radiation, Beta radiation, and combinations thereof.

57. The expandable intraluminal graft of claim 56, wherein said tubular member is treated with Gamma or Beta radiation to reduce the vascular narrowing of the stented section.

58. The expandable intraluminal graft of claim 50, wherein a plurality of said slots of said one set of slots include first and second ends, at least two adjacently positioned slots having said first and said seconds ends, said first ends of said slots lying in a first plane substantially parallel to a longitudinal axis of said body member when said body member is in said second diameter, said second ends of said slots lying in a second plane substantially parallel to a longitudinal axis of said body member when said body member is in said second diameter.

59. The expandable intraluminal graft of claim 58, wherein said material used to make the body visible under fluoroscopy is located on the outer surface of said body member at both ends of said body member.

60. The expandable intraluminal graft of claim 59, wherein at least a portion of said body member is treated with Gamma or Beta radiation.

61. The expandable intraluminal graft of claim 60, wherein said body member is a substantially tubular shaped member.

62. An expandable intraluminal graft for use within a body passageway, duct, blood vessel or other cavity-comprising:

a plurality of substantially tubular shaped member and at least one connector and two tubular shaped members, said connector connected between said two tubular shaped members, each of said tubular body members having first and second ends and a wall surface disposed between the first and second ends defining a longitudinal length of said tubular body members, said wall surface including a first and second set of slots about a circumference of each of said tubular body members, each set of slots including at least two slots positioned substantially parallel to one another and along said longitudinal length of each of said tubular body members;

each of said tubular shaped members having a first diameter which permits intraluminal delivery of said tubular shaped members into a body passageway, duct, blood vessel or other cavity, and a second expanded diameter which second diameter is variable, said tubular shaped members having substantially the same longitudinal length when said tubular shaped members are in their first diameter and in their said second diameter, said first set of slots not parallel to a longitudinal axis of said tubular shaped members when said tubular shaped members are in said first diameter, said first and said second set of slots forming an angle between said sets of slots between 0–90° when said tubular shaped members are in said first diameter, said second set of slots is not parallel to said longitudinal axis of said tubular shaped member when said tubular shaped member is in said first diameter, said first and second set of slots are not parallel to said longitudinal axis of said tubular shaped member when said tubular shaped member is in said second diameter;

said connector allowing transverse bending flexibility invariant to the plane of bending of said graft.

63. The expandable intraluminal graft of claim 62, wherein said tubular shaped member having material to make said tubular shaped member visible under fluoroscopy.

64. The expandable intraluminal graft of claim 63, wherein said tubular shaped member is treated with Gamma or Beta radiation to reduce the vascular narrowing of the stented section.

\* \* \* \* \*